United States Patent [19]
Plückthun et al.

[11] Patent Number: 5,910,573
[45] Date of Patent: Jun. 8, 1999

[54] MONOMERIC AND DIMERIC ANTIBODY-FRAGMENT FUSION PROTEINS

[75] Inventors: Andreas Plückthun; Peter Pack, both of München, Germany

[73] Assignee: Merck Patent Gesellschaft mit Beschrankter Haftung, Germany

[21] Appl. No.: 08/256,790

[22] PCT Filed: Jan. 15, 1993

[86] PCT No.: PCT/EP93/00082

§ 371 Date: Jul. 22, 1994

§ 102(e) Date: Jul. 22, 1994

[87] PCT Pub. No.: WO93/15210

PCT Pub. Date: Aug. 5, 1993

[30] Foreign Application Priority Data

Jan. 23, 1992 [EP] European Pat. Off. .............. 92101069

[51] Int. Cl.$^6$ .............................. C12P 21/08; C07K 16/46
[52] U.S. Cl. ..................... 530/387.3; 424/134.1; 424/185.1; 424/192.1; 424/130.1; 435/328; 436/547; 530/328
[58] Field of Search .................... 435/69.6, 328; 530/387.3, 328; 424/134.1, 185.1, 192.1, 130.1; 436/547

[56] References Cited

U.S. PATENT DOCUMENTS 5,132,405  7/1992  Huston et al. ...................... 530/387.3

FOREIGN PATENT DOCUMENTS 404097  12/1990  European Pat. Off. .

OTHER PUBLICATIONS

Bird et al., "Single Chain Antibody Variable Regions," Trends in Biotech., vol. 9, pp. 132–137 (Apr. 1991).

Blondel et al., "Engineering the Quaternary Structure of an Exported Protein with a Leucine Zipper," Protein Engineering, vol. 4, No. 4, pp. 457–461 (1991).

Pack et al., "Miniantibodies: Use of Amphipathic Helices to Produce Functional, Flexibly Linked Dimeric $F_v$ Fragments with High Avidity in *Escherichia coli*," Biochemistry, vol. 31, No. 6, pp. 1579–1584 (Feb. 18, 1992).

*Primary Examiner*—Toni R. Scheiner
*Assistant Examiner*—Timothy A. Worrall
*Attorney, Agent, or Firm*—Millen, White, Zelano, & Branigan, P.C.

[57] ABSTRACT

The present invention describes a new class of antigen binding molecules which contain Fv-fragments of an antibody but do not use the constant antibody domains. They can also dimerize with other antibody fragment molecules or with non-antibody fragment molecules to form bi- or multifunctional antibody-fragment fusion proteins and so-called miniantibodies, respectively. The new fusion proteins can be used in the broad field of diagnostic and therapeutical medicine.

19 Claims, 4 Drawing Sheets

MONOMERIC AND DIMERIC ANTIBODY-FRAGMENT FUSION PROTEINS

The present invention describes a new class of antigen binding molecules which contain Fv-fragments of an antibody but do not use the constant antibody domains. They can also dimerize with other antibody fragment molecules or with ace non-antibody fragment molecules to form bi- or multifunctional antibody-fragment fusion proteins and so-called mininantibodies, respectively. The new fusion proteins can be used in the broad field of diagnostic and therapeutical medicine.

BACKGROUND OF THE INVENTION

Since a few years there is a great interest in the biotechnological field to modify naturally occurring antibodies in order to obtain more specified and more individual antibody species. Therefore, attempts have been made to produce (modified) antibody fragments.

All naturally occurring antibodies of all classes have at least two binding sites. This enables them to bind to a surface with a greater functional affinity (also called avidity) than monovalent fragments, such as Fab fragments. Over the last few years, methods have been described (Skerra and Plückthun, 1988, Science 240, 1038–1040; Better et al., 1988, Science 240, 1041–1043) with which functional antibody fragments can be produced in *Escherichia coli*. These include the Fv fragment (the heterodimer consisting of $V_H$ and $V_L$) and the Fab fragment (consisting of the complete light chain with the domains $V_L$ and $C_L$ as well as the first two domains of the heavy chains $V_H$ and $C_{H1}$).

The Fv fragment, however, has a tendency to dissociate into $V_H$ and $V_L$ and therefore, it is advantageous to link the two domains covalently. One particular way of linking them is by designing a peptide linker between them, either in the orientation $V_H$-linker-$V_L$ or $V_L$-linker-$V_H$ (Bird et al.,1988, Science 242, 423; Huston et al., 1988, Proc. Natl. Acad. Sci. USA 85, 5879) The resulting fragments are called single-chain Fv fragments.

All these fragments are, however, monovalent. We describe in this invention a method to engineer small dimerization domains based on peptides forming amphipathic helices. These peptides will be referred to as "intercalating", but this term is only meant to express the ability of targeted association and not a restriction referring to a particular structure of the dimerization interface.

While the methodology described here, is in principle applicable to either Fab, Fv or scFv fragments, it is the latter for which their use is most advantageous. In this case bivalent fragments can be constructed of very small size, and still the dissociation into $V_L$ and $V_H$ as well as the wrong matching of fragment chains, e.g. $V_L$—$V_L$, can be prevented.

Antibody fragments of small size are of particular advantage in many applications. In diagnostic applications (e.g. ELISA, RIA, etc.), the smaller molecules surface decreases the problems of nonspecific interactions, which are known to frequently involve the constant domains. The same is true in using antibody fragments as ligands in affinity chromatography. In tumor diagnostics or therapy, it is important that a significant proportion of the injected antibody penetrates tissues and localizes to the tumor, and is dependent on the molecular dimensions (Colcher et al., 1990, J. Natl. Cancer Inst. 82, 1191–1197). Expression yields and secretion efficiency of recombinant proteins are also a function of chain size (Skerra & Plückthun, 1991, Protein Eng. 4, 971) and smaller proteins are preferred for this reason. Therefore, molecules of a small size are advantageous for several reasons.

Previously, decreasing the molecular dimensions of the antibody meant the preparation of proteolytic fragments. The smallest bivalent fragments, (Fab)'$_2$ fragments, are still about twice the size of the present fragments of this invention. Therefore, these new fragments combine three features: (a) small size, (b) bivalence or bifunctionality and (c) ability of functional expression in *E. coli*.

There is great interest in bifunctional antibodies in a large number of areas. Bifunctional antibodies may be defined as having two different specificities for either two different antigens or for two epitopes of the same antigen.

There are currently a number of methods how to produce bifunctional antibodies. However, none of the existing methods allows to produce exclusively bifunctional antibodies in vivo, but rather a mixture of molecular species always occur, requiring complicated and expensive separation procedures.

Four principal methods can be distinguished. In the first, chemical crosslinking is used, which may advantageously use heterobifunctional crosslinkers. By this method, whole antibodies (Staerz et al., 1985, Nature 314, 628; Perez et al, 1985, Nature 316, 354–356), Fab fragments (Carter et al., 1992, Biotechnology 10, 163) and scFv fragments (Cumber et al., 1992, J. Immunol. 149, 120) have been chemically crosslinked after purification.

The second previous method involved the fusion of two hybridomas to give a so-called heterohybridoma or "quadroma". In this method, any light chain can pair with any heavy chain, and the two heavy chains can give homodimers or heterodimers resulting in very complicated product mixtures (Milstein & Cuello, 1983, Nature 305, 537).

The third method is related to the second and consists of transfecting two expression plasmids into a hybridoma cell, encoding the heavy and light chain of the second antibody (Lenz & Weidle, 1990, Gene 87, 213) or a retroviral vector (De Monte et al., 1990, Acad. Sci. 87, 2941–2945). However, once introduced, the product mixture is identical as in the second procedure.

Finally, antibodies have been reduced, mixed and reoxidized (Staerz & Bevan, 1986, Immunology Today 7). Again, very complicated product mixtures are obtained requiring sophistical separation and quality control procedures.

Thus a method is still needed allowing the isolation of exclusively heterodimeric antibodies directly without the complicated preparation required from chemical crosslinking. In the present invention, this problem is solved by (i) covalently linking corresponding VH and VL domain in a scFv fragment and (ii) using dimerization domains only allowing the formation of heterodimers, such as certain leucine zippers and derivatives.

Another important consideration in the present invention was the desire to make the MW of the bispecific antibody as small as possible for reasons explained above in detail. This was achieved by using scFv fragments.

A number of uses of bispecific antibodies bave been described, and most of them would benefit from this new technology. For example, bispecific antibodies are of great interest in tumor therapy. One arm of the antibody may bind to a tumor marker, the other arm to a T-cell epitope, a toxin, or a radionuclide binding peptide or protein to bring a killing function close to the tumor cell. In diagnostics, one arm may bind to the analyte of interest and the other to a principle which can easily be quantified, e.g. an enzyme. Finally, in cellular applications, it may be advantageous to obtain higher selectivity in binding, if two different epitopes or the same protein complex can be recognized or if two different proteins can be recognized on the same cell surface.

Thus, it was object of the invention to create new individual and stable antibody fragment fusion proteins with bi- or even mulitfunctional binding sites.

It has been found that antibody fragment fusion proteins containing Fv-fragments could be produced by genetic engineering methods which show specified and improved properties.

Object of the invention is, therefore, a monomeric antibody-fragment fusion protein essentially consisting of a Fv-fragment of an antibody and a peptide which is capable to dimerize with another peptide by noncovalent interaction.

The term "noncovalent interaction" means every existing under normal condititions stable linkage which is not related to a covalent binding, for example linkage by Van der Waal's forces, (steric) interdigitation of amphiphilic peptides, especially peptide helices, or peptides bearing opposite charges of amino acid residues. The correspondingly effective peptides are called above and below interactive or intercalating peptides.

The amphiphilic peptides consist of up to 50 amino acids. Preferably they consist of 10 to 30 amino acids. In a preferred embodiment of the invention the interactive peptide is a peptide helix bundle (comprising of a helix, a turn and another helix, see above). In another embodiment the interactive peptide is a leucine zipper consisting of a peptide having several repeating amino acids, in which every seventh amino acid is a leucine residue. In other cases according to the invention the peptide bear positively or negatively charged residues, e.g. lysine (positively charged) or glutamic acid (negatively charged) in a way that this peptide can bind to another peptide (of a second monomeric unit) bearing opposite charges.

The Fv-fragment and the intercalating peptide are linked together either directly or by a linker peptide, preferably by a linker peptide. In a preferred embodiment the linker peptide is a hinge region sequence of an antibody.

As defined, the Fv-fragment consists of the $V_L$ and $V_H$ region of an antibody. The Fv-fragment according to the invention is preferably a single chain fragment. Single chain fragments can be obtained by standard techniques using standard linker molecules.

Furthermore, object of the invention is a dimeric fusion protein essentially consisting of two monomeric fusion proteins, wherein the linkage of the monomeric units bases on noncovalent interaction of identical or different peptides, characterized in that at least one monomeric unit is an antibody-Fv-fragment fusion protein as defined above.

If the dimer contains two Fv-fragments, the Fv-fragments may be the same (identical antigen binding sites) or may be different (different antigen binding sites). In these cases mono- and bispecific (Fv)-miniantibodies can be obtained. According to the invention bispecific mini-antibodies are preferred.

The interactive peptides may be the same or may be different; preferably, they are identical. The intercalating peptides may be associated in parallel or in antiparallel fashion.

Object of the invention is, therefore, above all, a dimeric fusion protein consisting of two Fv-fragments with different specificity (antigen binding sites) and identical intercalating helix peptides, the antibody fragments and the peptides are linked together by a hinge region sequence.

Furthermore, object of the invention is a dimer consisting of a monomeric unit containing a Fv-fragment and another monomeric unit wherein the Fv-Fragment was replaced by a non-antibody peptide. The non-antibody peptide may be a toxin, like ricin, a chelator- or metal binding peptide, or an enzyme (e.g. marker enzyme), or a peptide bearing a detectable label (e.g. a radioisotope).

The non-antibody peptide can also bear a corresponding binding site for said groups, binding sites directed to T-cells or T-cell fragments included.

Furthermore, the invention relates to monomers and diners, as defined above, wherein the interactive peptide(s) is (are) additionally fused at the C-terminus to target proteins/peptides as mentioned above, the corresponding binding sites included. Thus, the resulting fusion proteins and miniantibodies, respectively, are multifunctional.

The invention relates, furthermore, to a process for preparation of a monomeric antibody fusion protein as defined above, characterized in that the genes coding for the Fv-fragment, the interactive peptide and, if desired, the linking peptide are cloned into one expression plasmid, a host cell is transformed with said expression plasmid and cultivated in a nutrient solution, and the monomeric fusion protein is expressed in the cell or secreted into the medium.

Object of the invention is, finally, a process for preparation of a dimeric fusion protein as defined above, characterized in that the genes coding for the complete monomeric fusion proteins or parts of it are cloned at least into one expression plasmid, a host cell is transformed with said expression plasmid(s) and cultivated in a nutrient solution, and either the complete dimeric fusion protein is expressed in the cell or into the medium, or the monomeric fusion proteins are separately expressed and the noncovalent linkage between the two monomeric units is performed in the medium or in vitro, and in the case that only parts of the fusion proteins were cloned, protein engineering steps are additionally performed according to standard techniques.

The dimeric Fv-fragments containing fusion proteins according to the invention show a high avidity against corresponding antigens and a satisfying stability. These novel bivalent or bifunctional molecules can be prepared as folded and assembled molecules in *E. coli*. These miniantibodies are compatible with functional expression by secretion.

DETAILED DESCRIPTION OF THE INVENTION

Figure 1:
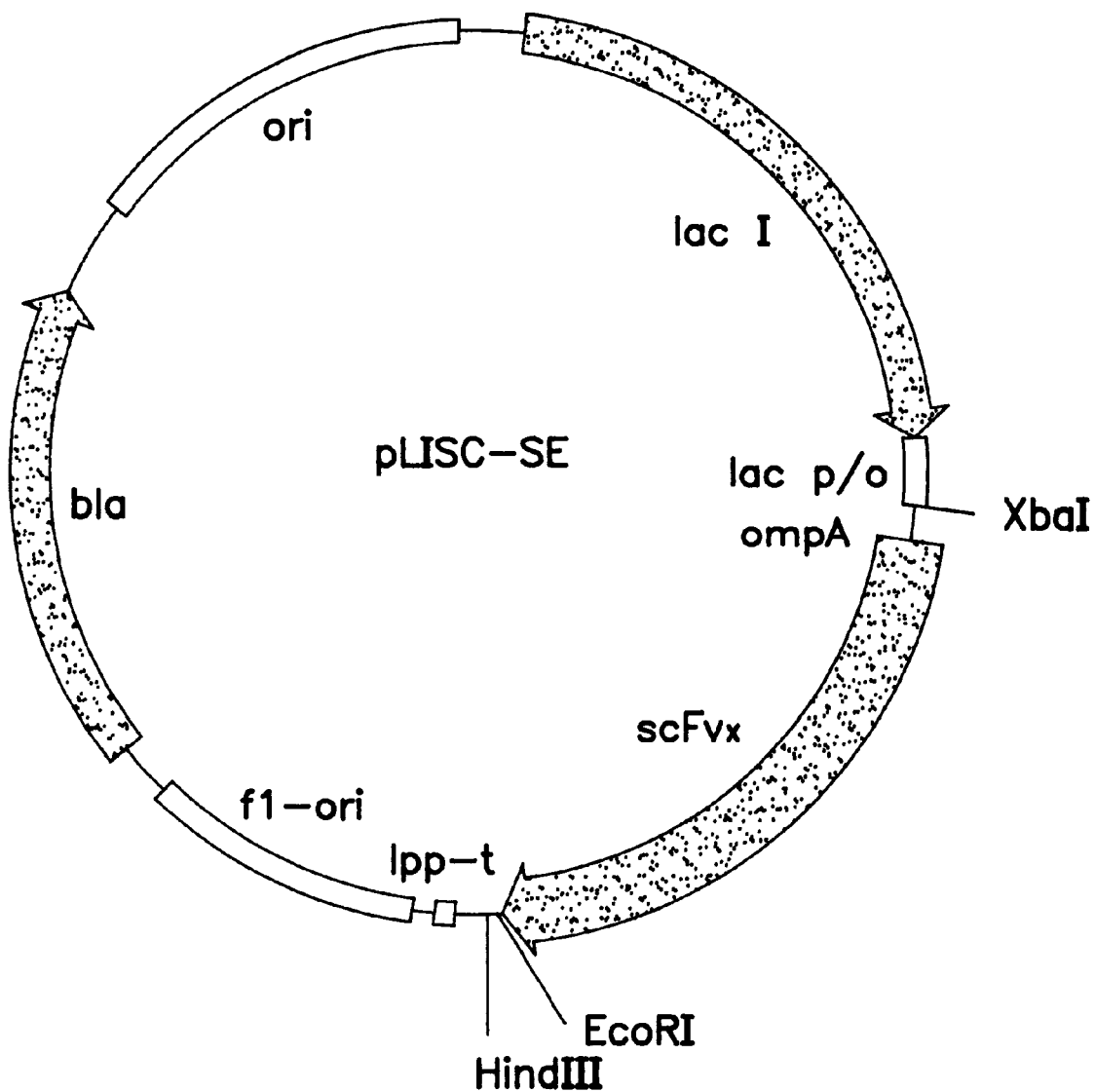

The oligomerization domains were selected for having a fairly small molecular weight and for being compatible with transport of the fusion protein through the membrane. They are based on two different types of amphiphilic helices.

Amphiphilic helices are known to predominantly, but not exclusively, associate in two different molecular structures: Four helix bundles and coiled coils. The design and formation of helix bundles has been studied previously (Eisenberg et al., 1986, Proteins 1, 16–22; Ho and deGrado, 1987, J. Am. Chem. Soc. 109, 6751–6758; Regan and deGrado, 1988, Science 241, 976–978; Hill et al., 1990, Science 294, 543–546). This molecule association is also known from natural proteins (Richardson, 1981, Adv. Prot. Chem. 34, 167).

The four helix bundle may be formed from either four separate molecules (each contributing one helix), two molecules containing two helices each (connected as helix-turn-helix) or one molecule containing a helix-turn-helix-turn-helix-turn-helix motif. For dimerization or multimerization, only the first two are suitable.

Three variations of this latter theme were tested. In the first, one helix of the sequence given in Eisenberg et al. (1986) (Proteins 1, 16–22) was used. In the second, this sequence was extended by a small hydrophilic peptide ending in a cysteine. Once the helices are associated, the hydrophilic peptides are held in sufficiently close contact that they can collide and a disulfide bond can form under oxidizing conditions, as in the periplasm of E. coli. In the third variation, two helices are used in tandem, separated by a short turn encoding peptide.

In the second design, peptides are used which can form so-called coiled-coil structures. Such peptides occur in transcription factors such as e.g. GCN4 from yeast and have been called leucine zippers (Landschulz et al., 1988, Science 240, 1759–1764). The crystal structure of this has been solved recently (O'Shea et al., 1991, Science 254, 539–544) and showed a parallel arrangement of the helices.

A covalent attachment of the helices is possible by a small peptide extension, again containing a cystein. Since the helices are now parallel, the peptide extension can be much shorter, since the distance is much smaller.

The various dimerization devices (intercalating helices) were however not fused to the antibody domain directly. It is advantageous to introduce a flexible peptide between the end of the scFv fragment and the beginning of the helix. As an example, the upper hinge region of mouse IgG3 has been used. However, a variety of hinges can be used. It is not required for dimerization per se, but provides a spacing of the two scFv domains similar to the antigen binding sites of a whole antibody. This way, the two binding sites span a greater distance in space and therefore can reach neighboring antigens on a solid surface.

The naturally occurring hinges of antibodies are preferred embodiments of hinges in bivalent miniantibodies. In the case of bifunctional miniantibodies, the hinges may be shorter, since frequently molecules from different surfaces are to be crosslinked as close as possible, and flexibility of the dimer is not necessary. The choice of the hinge is governed by the desired residue sequence, length (Argos, 1990, J. Mol. Biol. 211, 943–958), compatibility with folding and stability of the amphiphilic helices (Richardson & Richardson, 1988, Science 240, 1648–1652), secretion and resistance against proteases.

The present invention deals with peptides as dimerization devices, which should be as small as possible. One preferred embodiment is the use of peptides which can form amphipathic helices. Such helices shield the hydrophobic surface by dimerization or even multimerization. Helices of this type are characterized by their having hydrophobic patches on one face of the helix, and containing a sufficient number of helix-forming residues. Rules for such peptides are discussed in Eisenberg et al. 1986, O'Shea et al.,.1991 (Science 254, 539–544),1992 (Cell 68, 699–708).

Natural peptides of this type are found as the so-called leucine zippers, characterized by a periodic occurence of leucine (every seventh residue) and other hydrophilic residues (e.g. valine) also every seventh residue. As these principles are now understood (O'Shea et al. 1991, 1992, literature cited), the sequence can be varied to incorporate residues which make the association of homodimers unfavorable, but favors the association of heterodimers. Such sequence alteration can e.g. involve the incorporation of charge bridges, such that in the homodimers, like charges repel each other and in the heterodimer, opposite charges attract each other (see below).

The present invention can also be extended to bifunctional miniantibodies. In this case, dimerization devices (intercalation peptides) have to be used which will only allow the formation of heterodimers, but not homodimers. A preferred embodiment of this part of the invention are two different coiled-coil helices, such as in naturally occurring leucine zippers, e.g. from the transcription factor proteins jun and fos (O'Shea et al., 1989, Science 245, 646–648).

In a further embodiment of the invention, the constant scFv-hinge-helix can be extended at the C-terminus to result in a fusion protein. For example, a fusion to an enzyme may be made to use such bivalent constructs in diagnostics. Such enzymes are e.g. alkaline phosphatase, luciferase or horse radish peroxidase. The advantage of such a antibody-enzyme fusion protein would be that the bivalence of the antibody would lead to an enhanced binding to the surface-bound antigen. The advantage over a fusion protein prepared by conventional technology (i.e. chemical coupling of the antibody to the enzyme of choice) would be a greater batch-to-batch consistency; homogeneity of the product and the much simpler method of preparation, namely from E. coli in a single step.

In the same fashion, the miniantibodies may be extended at the C-terminus to incorporate a toxin. Such immunotoxins would be bivalent or even bispecific and thus combine the advantages of such antibody fragments linked above with the advantages in tumor therapy known for immunotoxins. Similarly, a metal binding peptide or protein could be linked genetically to be used in radioimmunotherapy or in tumor imaging. The same advantages for any genetically encoded hybrid protein hold true as given above for the antibody-enzyme fusions.

In another embodiment of the invention, a construct of the type scFv-hinge-helix may be made to dimerize with another protein fused to a dimerization domain, in complete analogy as described above for the formation of bispecific miniantibodies. In this fashion, the scFv fragment would e.g. be fitted with the helix of the fos protein. Such foreign protein, which could be made to form heterodimers with the scFv fragment, include enzymes useful in diagnosis, toxins, metal-binding peptides or proteins useful in radioimmunotherapy or radio-imaging.

Using the principles of this invention, the dimerization domains presented here can also serve for purification purposes. A recombinant protein of any kind can be fused to a dimerization domain, e.g. to hinge-fos-zipper. After coexpression with a scFv-hinge-jun, the heterodimer can be purified in one step with an affinity column for the scFv-specificity. In an alternative approach, the 'opposite' zipper, linked to a column support, 'catches' the protein-hinge-zipper when passing through the column as a crude cell extract.

The elution of the pure fusion protein from the column is possible using the unfolding temperature of the zipper. A subsequent separation from the dimerization domain is achievable by introduction of a proteolytic site, e.g. for blood clotting factor Xa, into the hinge (Nagai & Thogerson, 1987, Meth. Enzymol. 152,461–481).

A particular advantage of the miniantibodies described in this invention is the ability to assemble functionally in Escherichia coli. In the case of homobivalent constructs, a dimerization principle is used which allows the formation of homodimers. Examples described above include the coiled-coil helix (leucine zipper) of the yeast protein GCN4 or the helices from an antiparallel 4-helix bundle. In this case, the scFv fragment is expressed in the presence of a bacterial signal sequence and carries at the end of the gene of the scFv fragment the codons for a hinge and the dimerization helix or helix-turn-helix. The helices are compatible with secretion to the periplasmic space in E. coli, where protein folding, disulfide formation and assembly occurs. Under these conditions, the homodimeric proteins form by themselves and can directly be isolated in the dimeric form.

If heterobivalent constructs are desired, two different scFv fragments or one scFv fragment associating with a different protein need to associate. In the preferred embodiment of this invention, both proteins to be assembled are expressed in the same cell, preferably on the same plasmid, preferably as a dicistronic operon. The design of artificial dicistronic operons is explained e.g. in Skerra et al. (1991, Protein Eng. 4, 971). Since the assembly must take place in the periplasm, because the scFv fragment can only fold in the oxidizing milieu, both proteins must be transported and both must be fitted with a signal sequence. The dimerization peptides must be chosen such that they promote the association of two different proteins, but prevent the association of the respective homodimers. Examples of such proteins are the leucine zipper peptides of the proteins fos and jun (see above).

When not expressed in the same cell, the different scFv-hinge-zipper constructs have to be mixed together as a crude cell extract or purified protein and treated with raised temperature. In absence of the 'opposite' zipper, e.g. a scFv-hinge-jun-zipper construct is able to form homodimers. After short heating to the melting temperature of around 40~C, the zippers of the unwanted homodimer unfold and form a much more stable heterodimer (O'Shea et al., 1992, Cell 68, 699–708). Without raising the temperature, formation of heterodimers in vitro is not possible, as tested in experiments.

BRIEF DESCRIPTION OF THE FIGURES AND THE SEQUENCE LISTING

FIG. 1 scFv-Expression vector pLISC-SE containing the scFv-fragment.

Figure 2:
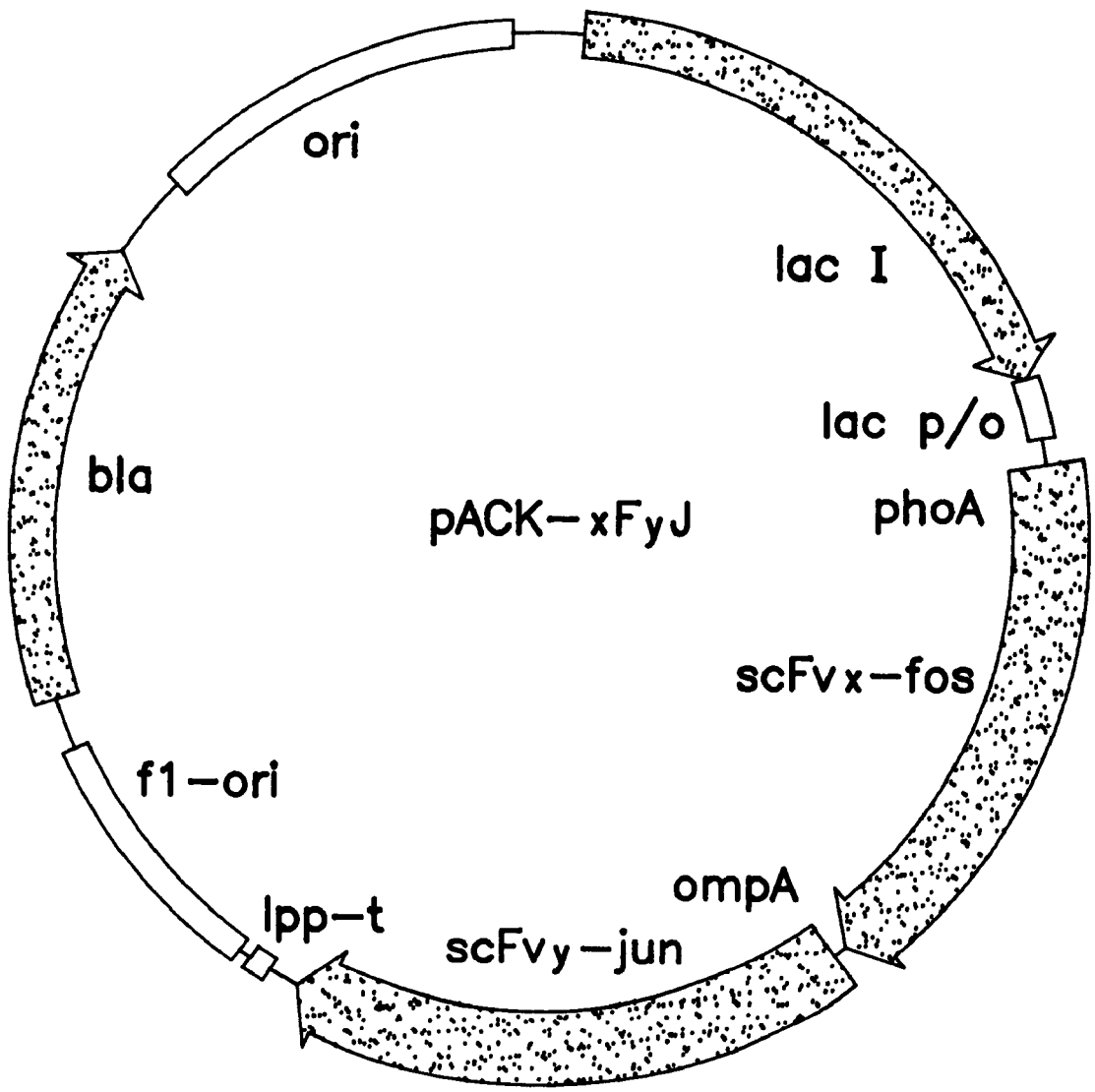

FIG. 2 Dicistronic scFv-hinge-zipper expression vector pACKxFyJ.

Figure 3A:
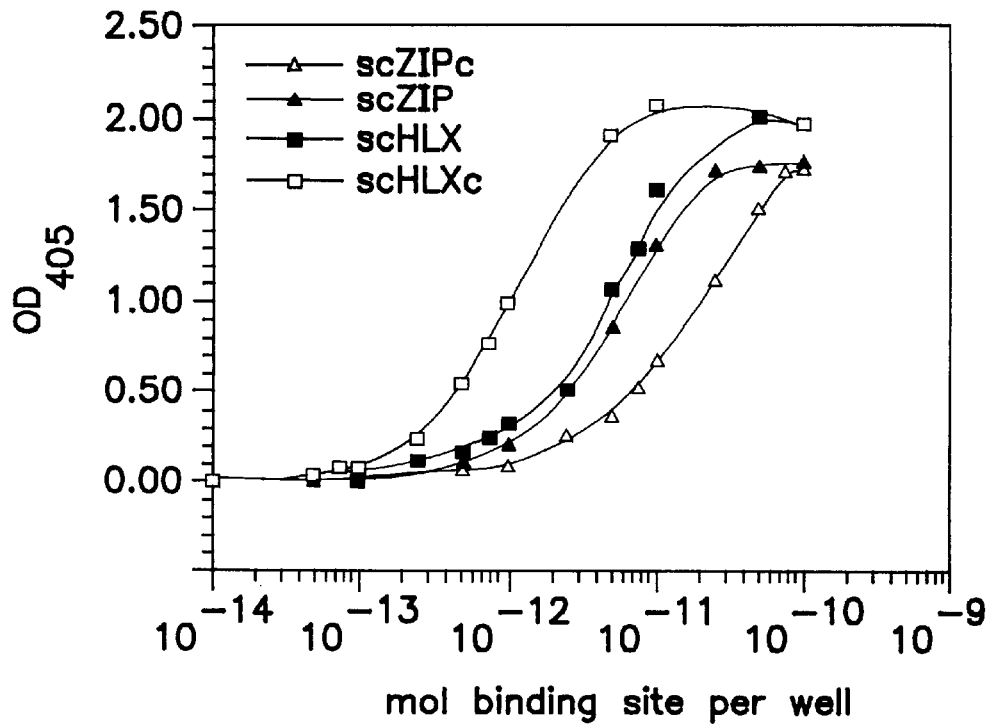
Figure 3B:
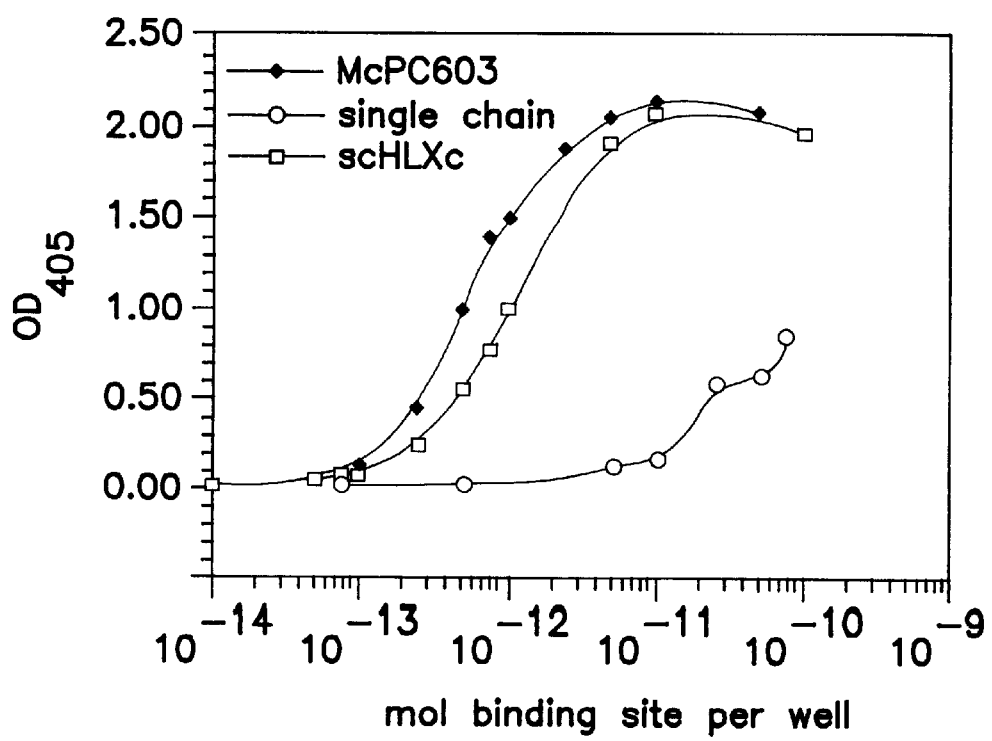

FIGS. 3a and 3b Functional ELISA; The concentrations of the affinity purified proteins, measured by $OD_{280}$ (vertical axis), refer to the molar number of binding sites per well (horizontal axis). The ELISA plates were coated with phosphocholine-BSA, and the purified phosphocholine-specific miniantibody-proteins were bound and detected by an anti-McPC603 antiserum. (3a) Comparison of various miniantibodies. (3b) Comparison of miniantibody scHLXc with ScFV and whole IgA.

Figure 4:
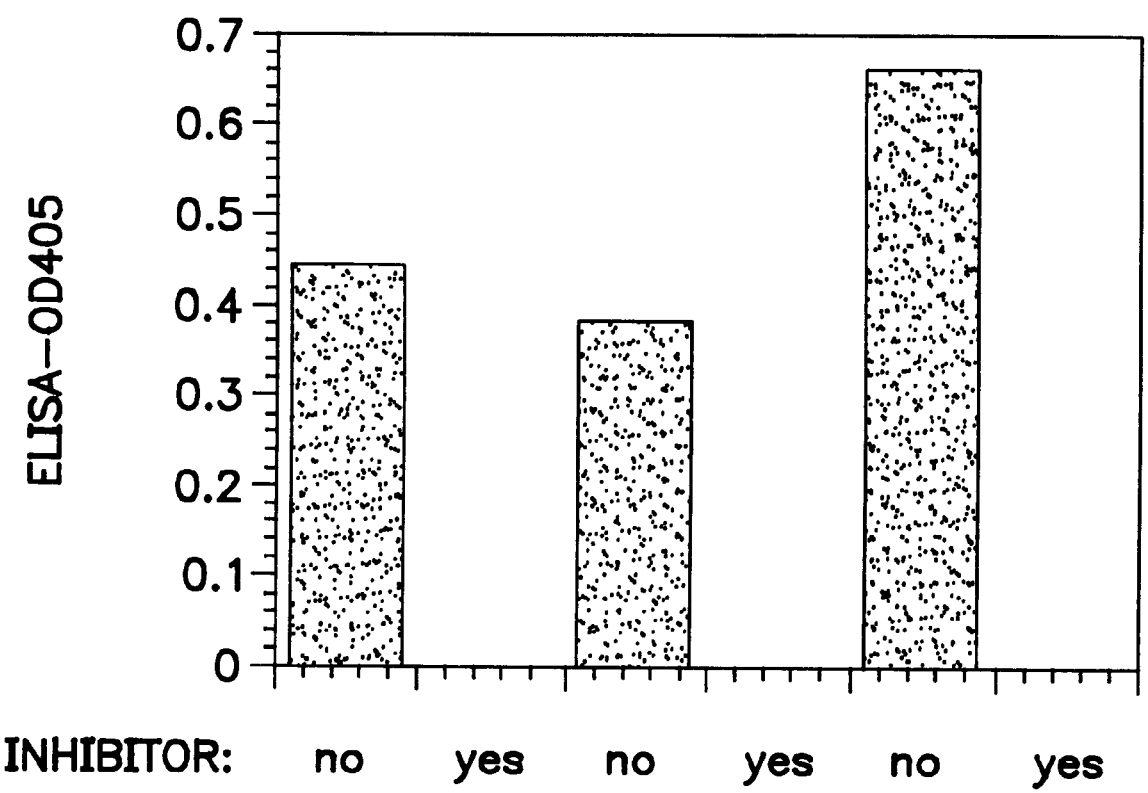

FIG. 4 Functional Anti-lysozyme ELISA; PC-affinity purified samples of coexpressed anti-PC-anti-lysozyme bispecific miniantibody. + and − on the horizontal axis means: plus inhibitor (+) and without inhibitor (−).

The attached sequence listing refers to sequence identity numbers (SEQ ID NO:):
SEQ ID NO:1–2 Whole nucleotid- and amino acid sequence of the pLISC-SE vector.
SEQ ID NO:3–4 Gene cassette of intercalating GCN4-leucine zipper (nucleotid- and amino acid sequence).
SEQ ID NO:5–6 Gene cassette encoding intercalating antiparallel helix-turn-helix (nucleotid- and amino acid sequence).
SEQ ID NO:7–8 Gene cassette encoding intercalating jun-zipper and IgG3-hinge region.
SEQ ID NO:9–10 Gene cassette encoding intercalating fos-zipper and IgG3-hinge region.
SEQ ID NO:11–12 Gene cassette encoding intercalating jun-zipper and designed linker.
SEQ ID NO:13–14 Gene cassette encoding intercalating fos-zipper and designed linker.

EXAMPLE 1

Construction of Vectors for Secreted Single-chain Fragments, Containing a Restriction Site for Introducing Genes for Intercalating Peptides.

Recombinant DNA-techniques were based on Sambrook et al. (1989, Molecular Cloning: A laboratory manual. Second edition. Cold Spring Harbor Laboratory, New York). Functional expression of the single-chain Fv fragments and the miniantibodies in E. coli JM83 was carried out with vectors similar to pASK-lisc (Skerra et al., 1991, Protein Eng. 4, 971). Site directed mutagenesis was directly performed in these vectors according to Kunkel et al. (1987, Meth. Enzymol. 154, 367–382) and Geisselsoder et al. (1987, Biotechniques 5, 786–791) using the helper phage M13K07 (Vieira & Messing, 1987, Meth. Enzymol. 153, 3–11). SDS-PAGE was carried out as described by Fling and Gregerson (1986, Anal. Biochem. 155, 83–88). Concentrations of affinity-purified proteins were measured by $OD_{280}$ using calculated extinction coefficients (Gill & von Hippel, 1989, Anal. Biochem. 182, 319–326).A vector such as pASK40 (Skerra et al., 1991, Protein Eng. 4, 971) is used, which contains an origin of replication, a regulatable promotor, a bacterial signal sequence followed by a multiple cloning site, a transcription terminator and an origin for single stranded phages. The gene for the single-chain Fv fragment is designed as follows: The nucleotide sequence of a $V_H$ domain is directly followed by a linker sequence encoding preferably about 15 residues, preferably of the sequence $(Gly_4Ser)_3$, followed directly by the sequence of the $V_L$ domain. Alternatively, the sequence of the $V_L$ domain may be directly followed by the sequence of the linker, followed by the sequence of the $V_H$ domain.

If the antibody is of known sequence, the complete gene of the scFv fragment may be assembled from synthetic oligonucleotides. A detailed experimental procedure for such a gene synthesis of an antibody gene is e.g. given in Plückthun et al. (1987, Cold Spring Harbor Symp. Quant. Biol. 52, 105–112).

If the genes of the $V_H$ and $V_L$ domains are present in other vectors, the gene for the scFv fragment may be assembled from restriction fragments. For example, a restriction fragment encoding most of the $V_H$ domain may be excised from another plasmid, and a fragment encoding most of the $V_L$ domain may be excised from a plasmid. The remaining pieces of $V_L$ and $V_H$ and the linker for the scFv fragment can be provided by cassettes of synthetic oligonucleotides, which need to be ligated by standard methodology (Sambrook et al., 1989, literature cited). The mixture of fragments is ligated into the vector pASK40 or a similar plasmid containing a pair of suitable restriction sites.

If the genes of the antibody have not been cloned before, they may be directly obtained from the hybridoma cell producing the antibody by the polymerase chain reaction (PCR; PCR methodology is described in McPherson et al., 1991, PCR-A Practical Approach Oxford University Press, New York). Primers suitable for amplification of $V_H$ and $V_L$ domains have been given by Orlandi et al., 1989, Proc. Natl. Acad. Sci. USA 86, 3833–3837; Huse et al., 1989, Science 246, 1275–1281; Larrick et al., 1989, Bio-technology 7, 934–938. The methodology of obtaining mRNA from hybridoma is described in these references as well. The separate $V_H$ and $V_L$ genes may be cloned into separate vectors, and the scFv gene assembled according to the principles explained above.

If the ligated fragments do not result in a correct reading frame of the scFv fragment, a precise fusion with the signal sequence codons resident on the plasmid may be generated by site directed mutagenesis. The design of the oligonucleotides and the execution is possible for anyone skilled in the art.

The scFv expression plasmid so obtained contains the codons for a bacterial signal sequence, directly followed by the first variable domain ($V_H$ or $V_L$), a linker and the second variable domain ($V_L$ or $V_H$) under the control of a regulatable promotor.

At the 3' end of this genes, corresponding to the C-terminus of the scFv protein, a unique restriction site is introduced into the expression plasmid to allow insertion of cassettes coding for the intercalating peptides. The restriction site is introduced by site directed mutagenesis using the method of Kunkel (1987, Meth. Enzymol. 154, 367–382).

An example of the complete sequence of a suitable single-chain Fv expression plasmid pLISC-SE for receiving an intercalation peptide is shown in FIG. 1 and Sequence Identity No. SEQ ID NO:1.

EXAMPLE 2
Design and Construction of a Gene Cassette Encoding Intercalating Peptides of a Leucine Zipper.

The gene cassette, fitted with restriction sites to be compatible with the restriction site at the 3' end of the scfv fragment gene, must encode the sequence of a hinge (connection the scFv fragment to the intercalating peptide) and the intercalation peptide itself. The hinge region, may however also be obmitted.

As an example the sequence of the upper hinge region of mouse IgG3 (Dangl et al., 1988, EMBO J. 7, 1989–1994), followed by the sequence of the leucine zipper sequence of the yeast protein GCN4 (Oas et al., 1990, Biochemistry T29, 2891–2894), is back-translated into frequently used E. coli codons SEQ ID NO:3 oligonucleotides are synthesized, and ligated into the vector pLISC-SE, previously digested with EcoRI and Hind III.

EXAMPLE 3
Design and Construction of a Gene Cassette Encoding Intercalating Peptides of a Four-helix Bundle.

Analogous to Example 2, the sequence of the upper hinge region of mouse IgG3, followed by the sequence of the helix-turn-helix of a four helix bundle (Eisenberg et al., 1986, literature cited) is backtranslated into frequently used E. coli codons (SEQ ID NO:5). Oligonucleotides are synthesized, and ligated into the vector pLISC-SE, previously digested with EcoRI and Hind III.

EXAMPLE 4
Design and Construction Two Gene Cassettes Encoding Intercalating Peptides of a Leucine Zipper and their Co-expression.

Analogous to Example 2, the sequence of the upper hinge region of mouse IgG3 followed by the sequence of the zipper sequence of the jun protein (O'Shea et al., 1992, literature cited), is backtranslated into frequently used E. coli codons (SEQ ID NO:7). Oligonucleotides are synthesized, and ligated into the vector pLISC-SE, previously digested with EcoRI and Hind III.

In a parallel reaction, the sequence of the upper hinge region of mouse IgG3, followed by the sequence of the zipper sequence of the fos protein (O'Shea et al., 1992, Cell 68, 699–708), is backtranslated into frequently used E. coli codons SEQ ID NO:9. Oligonucleotides are synthesized, and ligated into the vector pLISC-SE, previously digested with EcoRI and Hind III. The two vectors thus each code for a different antibody scFv fragment, followed by a hinge peptide and a different leucine zipper peptide. To co-express the two scFv fragments, the whole scFv-hinge-zipper gene of the fos-containing product is excised from the vector as a Xba I-Hind III fragment and ligated into the vector, pLISC-SE-scFv-jun, containing already the scFv gene of the other antibody.

The newly obtained vector then expresses the scFv$_1$-linker$_1$-fos-zipper and the scFv$_2$-linker$_2$-jun-zipper from a single promoter as a dicistronic operon.

An improved sequence for the hinge region in the context of jun and fos SEQ ID NO:12 and 14. This hinge is shorter and therefore not as susceptible to proteolysis. In cases, where the distance between the two binding sites is of less importance, such shortened hinges may be advantageous. In this case, the "tail" of the scFv fragment has been shortened and the EcoRI site, which receive the genes for the intercalating peptides has been moved four residues upstream.

EXAMPLE 5
Purification of Bivalent Miniantibody from E. coli.

E. coli JM83, harboring a plasmid constructed as in examples II and III, are grown to an O.D. 550 of 0.5 and induced with IPTG at a final concentration of 1 mM. The cells are centrifuged, resuspended in BBS buffer (200 mM Na-borate, 160 mM NaCl, pH 8.0) and the suspension is passed through a French press. In these examples, a phosphorylcholine binding miniantibody is used. The miniantibody is purified by passage over a phosphorylcholine affinity chromatography as described (Chesebro and Metzger, 1972, Biochemistry 11, 766–771)

EXAMPLE 6
Purification of a Bispecific Miniantibody from E. coli

E. coli JM83, harboring a plasmid constructed as in examples II and III and containing a dicistronic structural gene for two different scFv (FIG. 2), are grown to an O.D. 550 of 0.5 and induced with IPTG at a final concentration of 1 mM. The cells are centrifuged, resuspended in BBS buffer (200 mM Na-borate, 160 mM NaCl, pH 8.0) and the suspension is passed through a French press.

In this example, a bispecific miniantibody is used containing both a specificity for phosphorylcholine as well as benzoylampicillin. The miniantibody is purified by passage over a phosphorylcholine affinity chromatography as described (Chesebro and Metzger, 1972, literature cited)

EXAMPLE 7
Surface Binding of Bivalent Miniantibodies

The ELISA-plates (Nunc, Macrosorp) were coated with 400 ~g/ml phosphocholine-BSA in PBS buffer (20 mM phosphate, pH 7.2, 115 mM NaCl). The hapten reagent was prepared from nitrophenyl phosphocholine (Sigma), which was reduced and diazotized essentially as described (Chesebro & Metzger, 1972, literature cited), and reacted by azo-coupling to BSA (Sigma) in borate-saline buffer (52.5 mM sodium borate, pH 9, 120 mM NaCl) at 4°~C. for 48 hours with subsequent dialysis against PBS. After blocking the non-coated plate surface with 5% skim milk (Nestle) in PBS buffer for at least 2 hours, the periplasmic extract or the purified protein was incubated in BBS buffer on the plate for 90 min at room temperature. After thorough washing (3 times), remaining functional antibody fragments were detected according standard procedures (Harlow & Lane, 1988, "Antibodies, A Laboratory Manual", Cold Spring Harbor Laboratory, 555–592) with rabbit anti-McPC603 serum and anti-rabbit immunoglobulin linked to peroxidase (Sigma) according to Gallati (1979, Clin. Chem. Clin. Biochem. 17, 1–4).

An enormous gain in binding, and thus sensitivity, is observed for all miniantibody constructs, compared to the monomeric scFv fragment. This is consistent with the simultaneous binding of two or even more binding sites to the same surface. These avidity of the fusion protein scHLXc was comparable to the natural antibody McPC603, which could be detected with antigen-coated ELISA, while the monomeric scFv fragment could only be detected with hundred-fold higher concentrations (FIGS. 3a, b). All binding is nearly totally inhibitible with soluble hapten, except of the monomeric scFv fragment. The thermodynamic affinity of the natural antibody to soluble phosphocholine is about $1.6 \$ 10^5 M^{-1}$ and thus relatively weak (Metzger et al., 1971, Proceedings of the $I^{St}$ Congress of Imunology. Academic Press, New York, pp. 253–267), and this is apparently not sufficient for a monomeric fragment-hapten complex to survive the repeated washing steps of a functional ELISA (Kemeny & Challacombe, 1988, "ELISA and other solid phase immunoassays", Wiley & Sons, New York).

EXAMPLE 8
Surface Binding of Bifunctional Miniantibodies

Coexpressed functional miniantibodies recognizing phosphorylcholine with one arm and lysozyme with the other arm were purified by phosphocholine (PC) affinity chromatography and tested for lysozyme specificity. An ELISA-plate was coated with lysozyme, the ELISA was carried out as described in Example VII. Three different preparations show binding to the antigen-surface, which is completely inhibitible with soluble lysozyme (FIG. 4).

We claim:

1. A dimeric protein comprising two monomeric fusion proteins in a noncovalent interaction, wherein the orientation of the monomeric fusion proteins in the dimer is identical with respect to their N- and C-termini, the noncovalent interaction between monomeric fusion proteins is formed between interactive peptides on each monomeric fusion protein, which peptides are identical with each other or nonidentical, and each monomeric fusion protein is a monomeric antibody-fragment fusion protein comprising:
(a) a single chain Fv (scFv) fragment of an antibody,
(b) a linker peptide, and
(c) a first interactive peptide comprising a first amphiphilic helical peptide containing up to 50 amino acids, said first amphiphilic helical peptide being capable of forming a dimer with a second amphiphilic helical peptide by noncovalent interaction, wherein the C-terminus of (a) is fused with the N-terminus of (b), and the C-terminus of (b) is fused with the N-terminus of (c) and, with the proviso that if either monomeric fusion protein comprises a helical peptide which is a jun-zipper, the other monomeric fusion protein may not comprise a helical peptide which is a jun-zipper.

2. A dimeric protein of claim 1, wherein the interactive peptide in at least one of the monomeric fusion proteins of the dimeric protein comprises a helix, a turn and another helix.

3. A dimeric protein of claim 1, wherein the interactive peptide in at least one of the monomeric fusion proteins of the dimeric protein contains a leucine zipper molecule having several repeating amino acids, wherein every seventh amino acid is a leucine.

4. A dimeric protein of claim 1, wherein the interactive peptide in at least one of the monomeric fusion proteins of the dimeric protein bears charged residues.

5. A dimeric protein of claim 1, wherein the linker peptide in at least one of the monomeric fusion proteins of the dimeric protein is a hinge region sequence of an antibody or a fragment thereof.

6. A dimeric protein of claim 1, wherein the interactive peptides (c) on each monomeric fusion protein are identical.

7. A dimeric protein comprising a first monomeric fusion protein unit and a second monomeric fusion protein unit in a noncovalent interaction, wherein the noncovalent interaction between monomeric units is formed between interactive peptides on each monomeric unit, which peptides are identical with each other or nonidentical, each monomeric unit is an antibody-fragment fusion protein as set forth in claim 1 and the first monomeric unit and the second monomeric unit have different antigen-binding specificities.

8. A dimeric protein of claim 1, wherein another protein is fused at the C-terminus of one or both of the interactive peptides.

9. A process for preparation of a dimeric protein of claim 1, comprising cloning the DNA molecules having sequences coding for a monomeric fusion protein, or a part thereof, into at least one expression plasmid, transforming a host cell with said expression plasmid or plasmids, cultivating said transformed host cell in a nutrient medium, and either
(A) expressing the dimeric protein in the cell, or
(B) separately, expressing the monomeric fusion proteins or a part thereof, and forming the noncovalent linkage between the two monomeric fusion proteins in the medium or in vitro,
wherein when only a part of the fusion protein was cloned into one expression plasmid, the other part or parts of the fusion protein are assembled and fused in vitro with the cloned part to form the fusion protein, before or after forming the noncovalent linkage.

10. A process of claim 9, wherein the DNA sequence coding for the first monomeric fusion protein is cloned into a first expression plasmid, and the DNA sequence coding for the second monomeric fusion protein is cloned into a second expression plasmid.

11. A process of claim 9, wherein the noncovalent linkage between the monomeric fusion proteins forming the dimeric protein is formed in vitro.

12. A process of claim 9, wherein the host cell is E. coli.

13. A dimeric protein of claim 1, wherein the interactive peptides on each monomeric fusion protein in the dimer are nonidentical.

14. A dimeric protein of claim 13, wherein the interactive peptides on each monomeric fusion protein contain leucine zipper molecules, whereby the formation of heterodimers is favored.

15. A dimeric protein of claim 14, wherein the interactive peptide of one monomeric fusion protein contains a jun-zipper and the interactive peptide of the other monomeric fusion protein contains a fos-zipper.

16. A dimeric protein of claim 13, wherein the noncovalent interaction between the interactive peptides on each monomeric fusion protein is by intercalation.

17. A process of claim 9, further wherein, in step (A), the dimeric protein is secreted into the medium after expression.

18. A dimeric protein of claim 1, wherein the linker peptide is a hinge region.

19. A dimeric protein of claim 18, wherein the hinge region has an amino acid sequence selected from the group consisting of the hinge region sequences of SEQ ID NOS: 9–14.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 4515 base pairs
      (B) TYPE: nucleic acid
      (C) STRANDEDNESS: double
      (D) TOPOLOGY: circular (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
      (A) ORGANISM: synthetic, E. coli- and murine origin (vii) IMMEDIATE SOURCE:
      (B) CLONE: pLISC-SE (ix) FEATURE:
      (A) NAME/KEY: CDS
      (B) LOCATION: 1328..2158
      (D) OTHER INFORMATION: /product= "single chain Fv fragment
         (antibody)"
         /note= "complete sequence of the pLISC-SE vector"

(x) PUBLICATION INFORMATION:
      (A) AUTHORS: Plack, Peter
         Plueckthun, Andreas
      (B) TITLE: Miniantibodies: Use of Amphiphatic Helices to
         Produce Functional, Flexibly Linked Dimeric Fv
         Fragments with High Avidity in E. Coli
      (C) JOURNAL: Biochemistry
      (D) VOLUME: 31
      (E) ISSUE: 6
      (F) PAGES: 1579-1584
      (G) DATE: 1992

(xi) SEQUENCE DESCRIPTION: SEQ ID NO: 1:

```
ACCCGACACC ATCGAATGGC GCAAAACCTT TCGCGGTATG GCATGATAGC GCCCGGAAGA      60

GAGTCAATTC AGGGTGGTGA ATGTGAAACC AGTAACGTTA TACGATGTCG CAGAGTATGC     120

CGGTGTCTCT TATCAGACCG TTTCCCGCGT GGTGAACCAG GCCAGCCACG TTTCTGCGAA     180
```

-continued

```
AACGCGGGAA AAAGTGGAAG CGGCGATGGC GGAGCTGAAT TACATTCCCA ACCGCGTGGC    240

ACAACAACTG GCGGGCAAAC AGTCGTTGCT GATTGGCGTT GCCACCTCCA GTCTGGCCCT    300

GCACGCGCCG TCGCAAATTG TCGCGGCGAT TAAATCTCGC GCCGATCAAC TGGGTGCCAG    360

CTGTGTGGTG TCGATGGTAG AACGAAGCGG CGTCGAAGCC TGTAAAGCGG CGGTGCACAA    420

TCTTCTCGCG CAACGCGTCA GTGGGCTGAT CATTAACTAT CCGCTGGATG ACCAGGATGC    480

CATTGCTGTG GAAGCTGCCT GCACTAATGT TCCGGCGTTA TTTCTTGATG TCTCTGACCA    540

GACACCCATC AACAGTATTA TTTTCTCCCA TGAAGACGGT ACGCGACTGG GCGTGGAGCA    600

TCTGGTCGCA TTGGGTCACC AGCAAATCGC GCTGTTAGCG GGCCCATTAA GTTCTGTCTC    660

GGCGCGTCTG CGTCTGGCTG GCTGGCATAA ATATCTCACT CGCAATCAAA TTCAGCCGAT    720

AGCGGAACGG GAAGGCGACT GGAGTGCCAT GTCCGGTTTT CAACAAACCA TGCAAATGCT    780

GAATGAGGGC ATCGTTCCCA CTGCGATGCT GGTTGCCAAC GATCAGATGG CGCTGGGCGC    840

AATGCGCGCC ATTACCGAGT CCGGGCTGCG CGTTGGTGCG GATGTCTCGG TAGTGGGATA    900

CGCAGATACC GAAGACAGCT CATGTTATAT CCCGCCGTTA ACCACCATCA AACAGGATTT    960

TCGCCTGCTG GGGCAAACCA GCGTGGACCG CTTGCTGCAA CTCTCTCAGG GCCAGGCGGT   1020

GAAGGGCAAT CAGCTGTTGC CCGTCTCACT GGTGAAAAGA AAAACCACCC TGGCGCCCAA   1080

TACGCAAACC GCCTCTCCCC GCGCGTTGGC CGATTCATTA ATGCAGCTGG CACGACAGGT   1140

TTCCCGACTG GAAAGCGGGC AGTGAGCGCA ACGCAATTAA TGTGAGTTAG CTCACTCATT   1200

AGGCACCCCA GGCTTTACAC TTTATGCTTC CGGCTCGTAT GTTGTGTGGA ATTGTGAGCG   1260

GATAACAATT TCACACAGGA AACAGCTATG ACCATGATTA CGAATTTCTA GATAACGAGG   1320

GCAAAAA ATG AAA AAG ACA GCT ATC GCG ATT GCA GTG GCA CTG GCT GGT   1369
        Met Lys Lys Thr Ala Ile Ala Ile Ala Val Ala Leu Ala Gly
          1               5                  10

TTC GCT ACC GTA GCG CAG GCC GAA GTT AAA CTG GTA GAG TCT GGT GGT   1417
Phe Ala Thr Val Ala Gln Ala Glu Val Lys Leu Val Glu Ser Gly Gly
 15              20                  25                  30

GGT CTG GTA CAG CCG GGT GGA TCC CTG CGT CTG TCT TGC GCT ACC TCA   1465
Gly Leu Val Gln Pro Gly Gly Ser Leu Arg Leu Ser Cys Ala Thr Ser
                 35                  40                  45

GGT TTC ACC TTC TCT GAC TTC TAC ATG GAG TGG GTA CGT CAG CCC CCG   1513
Gly Phe Thr Phe Ser Asp Phe Tyr Met Glu Trp Val Arg Gln Pro Pro
                 50                  55                  60

GGT AAA CGT CTC GAG TGG ATC GCA GCT AGC CGT AAC AAA GGT AAC AAG   1561
Gly Lys Arg Leu Glu Trp Ile Ala Ala Ser Arg Asn Lys Gly Asn Lys
         65                  70                  75

TAT ACC ACC GAA TAC AGC GCT TCT GTT AAA GGT CGT TTC ATC GTT TCT   1609
Tyr Thr Thr Glu Tyr Ser Ala Ser Val Lys Gly Arg Phe Ile Val Ser
     80                  85                  90

CGT GAC ACT AGT CAA TCG ATC CTG TAC CTG CAG ATG AAT GCA TTG CGT   1657
Arg Asp Thr Ser Gln Ser Ile Leu Tyr Leu Gln Met Asn Ala Leu Arg
 95                  100                 105                 110

GCT GAA GAC ACC GCT ATC TAC TAC TGC GCG CGT AAC TAC TAT GGC AGC   1705
Ala Glu Asp Thr Ala Ile Tyr Tyr Cys Ala Arg Asn Tyr Tyr Gly Ser
                 115                 120                 125

ACT TGG TAC TTC GAC GTT TGG GGT GCA GGT ACC ACC GTT ACC GTT TCT   1753
Thr Trp Tyr Phe Asp Val Trp Gly Ala Gly Thr Thr Val Thr Val Ser
                 130                 135                 140

TCT GGT GGT GGT GGT TCT GGT GGT GGT GGT TCT GGT GGT GGT GGT TCT   1801
Ser Gly Gly Gly Gly Ser Gly Gly Gly Gly Ser Gly Gly Gly Gly Ser
                 145                 150                 155

GAT ATC GTT ATG ACC CAG TCT CCG AGC TCT CTG TCT GTA TCT GCA GGT   1849
Asp Ile Val Met Thr Gln Ser Pro Ser Ser Leu Ser Val Ser Ala Gly
```

```
                160                 165                  170
GAA CGT GTT ACC ATG TCT TGC AAA TCT TCT CAG TCT CTG CTG AAC TCT      1897
Glu Arg Val Thr Met Ser Cys Lys Ser Ser Gln Ser Leu Leu Asn Ser
175                 180                 185                 190

GGT AAC CAG AAA AAC TTC CTG GCG TGG TAT CAG CAA AAG CCT GGC CAA      1945
Gly Asn Gln Lys Asn Phe Leu Ala Trp Tyr Gln Gln Lys Pro Gly Gln
                195                 200                 205

CCG CCG AAA CTG CTG ATC TAC GGT GCG TCG ACC CGT GAA TCT GGT GTT      1993
Pro Pro Lys Leu Leu Ile Tyr Gly Ala Ser Thr Arg Glu Ser Gly Val
            210                 215                 220

CCG GAC CGT TTT ACC GGT AGC GGT AGC GGT ACC GAC TTC ACT CTG ACC      2041
Pro Asp Arg Phe Thr Gly Ser Gly Ser Gly Thr Asp Phe Thr Leu Thr
            225                 230                 235

ATC TCT TCT GTA CAG GCT GAA GAT CTG GCT GTT TAC TAC TGT CAA AAC      2089
Ile Ser Ser Val Gln Ala Glu Asp Leu Ala Val Tyr Tyr Cys Gln Asn
        240                 245                 250

GAC CAC TCT TAC CCG CTG ACC TTT GGC GCC GGC ACC AAA CTG GAA CTG      2137
Asp His Ser Tyr Pro Leu Thr Phe Gly Ala Gly Thr Lys Leu Glu Leu
255                 260                 265                 270

AAG CGC GCT AAC GGT GAA TTC TGATAAGCTT GACCTGTGAA GTGAAAATG          2188
Lys Arg Ala Asn Gly Glu Phe
                275

GCGCACATTG TGCGACATTT TTTTTGTCTG CCGTTTACCG CTACTGCGTC ACGGATCCCC    2248

ACGCGCCCTG TAGCGGCGCA TTAAGCGCGG CGGGTGTGGT GGTTACGCGC AGCGTGACCG    2308

CTACACTTGC CAGCGCCCTA GCGCCCGCTC CTTTCGCTTT CTTCCCTTCC TTTCTCGCCA    2368

CGTTCGCCGG CTTTCCCCGT CAAGCTCTAA ATCGGGGCAT CCCTTTAGGG TTCCGATTTA    2428

GTGCTTTACG GCACCTCGAC CCCAAAAAAC TTGATTAGGG TGATGGTTCA CGTAGTGGGC    2488

CATCGCCCTG ATAGACGGTT TTTCGCCCTT TGACGTTGGA GTCCACGTTC TTTAATAGTG    2548

GACTCTTGTT CCAAACTGGA ACAACACTCA ACCCTATCTC GGTCTATTCT TTTGATTTAT    2608

AAGGGATTTT GCCGATTTCG GCCTATTGGT TAAAAAATGA GCTGATTTAA CAAAAATTTA    2668

ACGCGAATTT TAACAAAATA TTAACGTTTA CAATTTCAGG TGGCACTTTT CGGGGAAATG    2728

TGCGCGGAAC CCCTATTTGT TTATTTTTCT AAATACATTC AAATATGTAT CCGCTCATGA    2788

GACAATAACC CTGATAAATG CTTCAATAAT ATTGAAAAAG GAAGAGTATG AGTATTCAAC    2848

ATTTCCGTGT CGCCCTTATT CCCTTTTTTG CGGCATTTTG CCTTCCTGTT TTTGCTCACC    2908

CAGAAACGCT GGTGAAAGTA AAAGATGCTG AAGATCAGTT GGGTGCACGA GTGGGTTACA    2968

TCGAACTGGA TCTCAACAGC GGTAAGATCC TTGAGAGTTT TCGCCCCGAA GAACGTTTTC    3028

CAATGATGAG CACTTTTAAA GTTCTGCTAT GTGGCGCGGT ATTATCCCGT ATTGACGCCG    3088

GGCAAGAGCA ACTCGGTCGC CGCATACACT ATTCTCAGAA TGACTTGGTT GAGTACTCAC    3148

CAGTCACAGA AAAGCATCTT ACGGATGGCA TGACAGTAAG AGAATTATGC AGTGCTGCCA    3208

TAACCATGAG TGATAACACT GCGGCCAACT TACTTCTGAC AACGATCGGA GGACCGAAGG    3268

AGCTAACCGC TTTTTTGCAC AACATGGGGG ATCATGTAAC TCGCCTTGAT CGTTGGGAAC    3328

CGGAGCTGAA TGAAGCCATA CCAAACGACG AGCGTGACAC CACGATGCCT GTAGCAATGG    3388

CAACAACGTT GCGCAAACTA TTAACTGGCG AACTACTTAC TCTAGCTTCC CGGCAACAAT    3448

TAATAGACTG GATGGAGGCG GATAAAGTTG CAGGACCACT TCTGCGCTCG GCCCTTCCGG    3508

CTGGCTGGTT TATTGCTGAT AAATCTGGAG CCGGTGAGCG TGGGTCTCGC GGTATCATTG    3568

CAGCACTGGG GCCAGATGGT AAGCCCTCCC GTATCGTAGT TATCTACACG ACGGGGAGTC    3628

AGGCAACTAT GGATGAACGA AATAGACAGA TCGCTGAGAT AGGTGCCTCA CTGATTAAGC    3688
```

```
ATTGGTAACT GTCAGACCAA GTTTACTCAT ATATACTTTA GATTGATTTA AAACTTCATT      3748

TTTAATTTAA AAGGATCTAG GTGAAGATCC TTTTTGATAA TCTCATGACC AAAATCCCTT      3808

AACGTGAGTT TTCGTTCCAC TGAGCGTCAG ACCCCGTAGA AAAGATCAAA GGATCTTCTT      3868

GAGATCCTTT TTTTCTGCGC GTAATCTGCT GCTTGCAAAC AAAAAAACCA CCGCTACCAG      3928

CGGTGGTTTG TTTGCCGGAT CAAGAGCTAC CAACTCTTTT TCCGAAGGTA ACTGGCTTCA      3988

GCAGAGCGCA GATACCAAAT ACTGTCCTTC TAGTGTAGCC GTAGTTAGGC CACCACTTCA      4048

AGAACTCTGT AGCACCGCCT ACATACCTCG CTCTGCTAAT CCTGTTACCA GTGGCTGCTG      4108

CCAGTGGCGA TAAGTCGTGT CTTACCGGGT TGGACTCAAG ACGATAGTTA CCGGATAAGG      4168

CGCAGCGGTC GGGCTGAACG GGGGGTTCGT GCACACAGCC CAGCTTGGAG CGAACGACCT      4228

ACACCGAACT GAGATACCTA CAGCGTGAGC TATGAGAAAG CGCCACGCTT CCCGAAGGGA      4288

GAAAGGCGGA CAGGTATCCG GTAAGCGGCA GGGTCGGAAC AGGAGAGCGC ACGAGGGAGC      4348

TTCCAGGGGG AAACGCCTGG TATCTTTATA GTCCTGTCGG GTTTCGCCAC CTCTGACTTG      4408

AGCGTCGATT TTTGTGATGC TCGTCAGGGG GGCGGAGCCT ATGGAAAAAC GCCAGCAACG      4468

CGGCCTTTTT ACGGTTCCTG GCCTTTTGCT GGCCTTTTGC TCACATG                   4515
```

(2) INFORMATION FOR SEQ ID NO: 2:

(i) SEQUENCE CHARACTERISTICS:
        (A) LENGTH: 277 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Lys Thr Ala Ile Ala Ile Ala Val Ala Leu Ala Gly Phe Ala
  1               5                  10                  15

Thr Val Ala Gln Ala Glu Val Lys Leu Val Glu Ser Gly Gly Gly Leu
             20                  25                  30

Val Gln Pro Gly Gly Ser Leu Arg Leu Ser Cys Ala Thr Ser Gly Phe
         35                  40                  45

Thr Phe Ser Asp Phe Tyr Met Glu Trp Val Arg Gln Pro Pro Gly Lys
     50                  55                  60

Arg Leu Glu Trp Ile Ala Ala Ser Arg Asn Lys Gly Asn Lys Tyr Thr
 65                  70                  75                  80

Thr Glu Tyr Ser Ala Ser Val Lys Gly Arg Phe Ile Val Ser Arg Asp
                 85                  90                  95

Thr Ser Gln Ser Ile Leu Tyr Leu Gln Met Asn Ala Leu Arg Ala Glu
            100                 105                 110

Asp Thr Ala Ile Tyr Tyr Cys Ala Arg Asn Tyr Tyr Gly Ser Thr Trp
        115                 120                 125

Tyr Phe Asp Val Trp Gly Ala Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Val Met Thr Gln Ser Pro Ser Ser Leu Ser Val Ser Ala Gly Glu Arg
                165                 170                 175

Val Thr Met Ser Cys Lys Ser Ser Gln Ser Leu Leu Asn Ser Gly Asn
            180                 185                 190

Gln Lys Asn Phe Leu Ala Trp Tyr Gln Gln Lys Pro Gly Gln Pro Pro
        195                 200                 205

Lys Leu Leu Ile Tyr Gly Ala Ser Thr Arg Glu Ser Gly Val Pro Asp
```

```
                210                 215                 220
Arg Phe Thr Gly Ser Gly Ser Gly Thr Asp Phe Thr Leu Thr Ile Ser
225                 230                 235                 240

Ser Val Gln Ala Glu Asp Leu Ala Val Tyr Tyr Cys Gln Asn Asp His
                245                 250                 255

Ser Tyr Pro Leu Thr Phe Gly Ala Gly Thr Lys Leu Glu Leu Lys Arg
                260                 265                 270

Ala Asn Gly Glu Phe
                275
```

(2) INFORMATION FOR SEQ ID NO: 3:

(i) SEQUENCE CHARACTERISTICS:
        (A) LENGTH: 151 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
        (A) ORGANISM: synthetic (deduced from yeast + mouse
            sequences)

(ix) FEATURE:
        (A) NAME/KEY: CDS
        (B) LOCATION: 1..138
        (D) OTHER INFORMATION: /product= "intercalating peptide"
            /note= "Gene cassette of intercalating
            GCN4-leucine zipper"

(ix) FEATURE:
        (A) NAME/KEY: misc_feature
        (B) LOCATION: 10..39
        (D) OTHER INFORMATION: /product= "Immunoglobulin Joining
            Region"
            /note= "IgG3-hinge"

(ix) FEATURE:
        (A) NAME/KEY: misc_feature
        (B) LOCATION: 40..138
        (D) OTHER INFORMATION: /product= "GCN4-zipper"

(xi) SEQUENCE DESCRIPTION: SEQ ID NO: 3:

```
GGT GAA TTC CCC AAA CCT AGT ACT CCC CCT GGC AGC AGC CGC ATG AAA         48
Gly Glu Phe Pro Lys Pro Ser Thr Pro Pro Gly Ser Ser Arg Met Lys
  1               5                  10                  15

CAG CTG GAA GAT AAA GTT GAA GAG CTT CTT TCG AAA AAC TAC CAC CTC         96
Gln Leu Glu Asp Lys Val Glu Glu Leu Leu Ser Lys Asn Tyr His Leu
                 20                  25                  30

GAA AAT GAA GTT GCG CGC CTC AAA AAA CTT GTT GGT GAA CGC                138
Glu Asn Glu Val Ala Arg Leu Lys Lys Leu Val Gly Glu Arg
             35                  40                  45

TGATAAGCTT GAC                                                         151
```

(2) INFORMATION FOR SEQ ID NO: 4:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO: 4:

Gly Glu Phe Pro Lys Pro Ser Thr Pro Pro Gly Ser Ser Arg Met Lys
1               5                   10                  15

Gln Leu Glu Asp Lys Val Glu Glu Leu Leu Ser Lys Asn Tyr His Leu
            20                  25                  30

Glu Asn Glu Val Ala Arg Leu Lys Lys Leu Val Gly Glu Arg
        35                  40                  45

(2) INFORMATION FOR SEQ ID NO: 5:

(i) SEQUENCE CHARACTERISTICS:
        (A) LENGTH: 181 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
        (A) ORGANISM: synthetic (ix) FEATURE:
        (A) NAME/KEY: CDS
        (B) LOCATION: 1..150
        (D) OTHER INFORMATION: /product= "intercalating peptide"
            /note= "Gene casette encoding intercalating
            antiparallel helix-turn-helix"

(ix) FEATURE:
        (A) NAME/KEY: misc_feature
        (B) LOCATION: 10..39
        (D) OTHER INFORMATION: /product= "Immunoglobulin Joining
            Region"
            /note= "IgG3-hinge"

(ix) FEATURE:
        (A) NAME/KEY: misc_feature
        (B) LOCATION: 40..87
        (D) OTHER INFORMATION: /product= "helix peptide"
            /note= "bundle-helix A"

(ix) FEATURE:
        (A) NAME/KEY: misc_feature
        (B) LOCATION: 88..150
        (D) OTHER INFORMATION: /product= "helix peptide"
            /note= "bundle-helix B"

(xi) SEQUENCE DESCRIPTION: SEQ ID NO: 5:

GGT GAA TTC CCC AAA CCT AGC ACC CCC CCT GGC AGC AGT GGT GAA CTG      48
Gly Glu Phe Pro Lys Pro Ser Thr Pro Pro Gly Ser Ser Gly Glu Leu
1               5                   10                  15

GAA GAG CTG CTT AAG CAT CTT AAA GAA CTT CTG AAG GGC CCC CGC AAA      96
Glu Glu Leu Leu Lys His Leu Lys Glu Leu Leu Lys Gly Pro Arg Lys
            20                  25                  30

GGC GAA CTC GAG GAA CTG CTG AAA CAT CTG AAG GAG CTG CTT AAA GGT    144
Gly Glu Leu Glu Glu Leu Leu Lys His Leu Lys Glu Leu Leu Lys Gly
        35                  40                  45

GAA TTC TGATAAGCTT GACCTGTGAA GTGAAAAAAT G                     181
Glu Phe
    50

(2) INFORMATION FOR SEQ ID NO: 6:

(i) SEQUENCE CHARACTERISTICS:
        (A) LENGTH: 50 amino acids (B) TYPE: amino acid
(D) TOPOLOGY: linear (ii) MOLECULE TYPE: protein (xi) SEQUENCE DESCRIPTION: SEQ ID NO: 6:

```
Gly Glu Phe Pro Lys Pro Ser Thr Pro Pro Gly Ser Ser Gly Glu Leu
 1               5                  10                  15

Glu Glu Leu Leu Lys His Leu Lys Glu Leu Leu Lys Gly Pro Arg Lys
            20                  25                  30

Gly Glu Leu Glu Glu Leu Leu Lys His Leu Lys Glu Leu Leu Lys Gly
        35                  40                  45

Glu Phe
    50
```

(2) INFORMATION FOR SEQ ID NO: 7:

(i) SEQUENCE CHARACTERISTICS:
      (A) LENGTH: 180 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
      (A) ORGANISM: synthetic, deduced from human and murine
          sequences (ix) FEATURE:
      (A) NAME/KEY: CDS
      (B) LOCATION: 1..159
      (D) OTHER INFORMATION: /product= "intercalating peptide"
          /note= "gene cassette encoding intercalating
          jun-zipper and IgG3-hinge reg..."

(ix) FEATURE:
      (A) NAME/KEY: misc_feature
      (B) LOCATION: 10..39
      (D) OTHER INFORMATION: /product= "Immunoglobulin Joining
         Region"
          /note= "IgG3-hinge region (mouse)"

(ix) FEATURE:
      (A) NAME/KEY: misc_feature
      (B) LOCATION: 40..159
      (D) OTHER INFORMATION: /product= "jun-zipper"

(xi) SEQUENCE DESCRIPTION: SEQ ID NO: 7:

```
GGT GAA TTC CCC AAA CCT AGT ACT CCC CCT GGC AGC AGC CGT ATC GCT        48
Gly Glu Phe Pro Lys Pro Ser Thr Pro Pro Gly Ser Ser Arg Ile Ala
 1               5                  10                  15

CGT CTC GAG GAA AAA GTT AAA ACC CTG AAA GCT CAG AAC TCC GAA CTG        96
Arg Leu Glu Glu Lys Val Lys Thr Leu Lys Ala Gln Asn Ser Glu Leu
            20                  25                  30

GCT TCC ACC GCT AAC ATG CTG CGT GAA CAG GTT GCT CAG CTG AAA CAG       144
Ala Ser Thr Ala Asn Met Leu Arg Glu Gln Val Ala Gln Leu Lys Gln
        35                  40                  45

AAA GTT ATG AAC TAC TGATAAGCTT GACCTGTGAA G                            180
Lys Val Met Asn Tyr
    50
```

(2) INFORMATION FOR SEQ ID NO: 8:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 8:

Gly Glu Phe Pro Lys Pro Ser Thr Pro Pro Gly Ser Ser Arg Ile Ala
 1               5                  10                  15

Arg Leu Glu Glu Lys Val Lys Thr Leu Lys Ala Gln Asn Ser Glu Leu
             20                  25                  30

Ala Ser Thr Ala Asn Met Leu Arg Glu Gln Val Ala Gln Leu Lys Gln
         35                  40                  45

Lys Val Met Asn Tyr
     50

(2) INFORMATION FOR SEQ ID NO: 9:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
        (A) ORGANISM: synthetic, deduced from human and murine
            sequences (ix) FEATURE:
        (A) NAME/KEY: CDS
        (B) LOCATION: 1..159
        (D) OTHER INFORMATION: /product= "intercalating peptide"
            /note= "gene cassette encoding intercalating
            fos-zipper and IgG3-hinge"

(ix) FEATURE:
        (A) NAME/KEY: misc_feature
        (B) LOCATION: 10..39
        (D) OTHER INFORMATION: /product= "Immunoglobulin Joining
            Region"
            /note= "IgG3-hinge (mouse)"

(ix) FEATURE:
        (A) NAME/KEY: misc_feature
        (B) LOCATION: 40..159
        (D) OTHER INFORMATION: /product= "fos-zipper"

(xi) SEQUENCE DESCRIPTION: SEQ ID NO: 9:

GGT GAA TTC CCC AAA CCT AGT ACT CCC CCT GGC AGC AGC CTG ACC GAC        48
Gly Glu Phe Pro Lys Pro Ser Thr Pro Pro Gly Ser Ser Leu Thr Asp
 1               5                  10                  15

ACC CTG CAG GCT GAA ACC GAC CAG CTG GAA GAC AAA AAA TCC GCT CTG        96
Thr Leu Gln Ala Glu Thr Asp Gln Leu Glu Asp Lys Lys Ser Ala Leu
             20                  25                  30

CAG ACC GAA ATC GCT AAC CTG CTG AAA GAA AAA GAA AAA CTG GAA TTT       144
Gln Thr Glu Ile Ala Asn Leu Leu Lys Glu Lys Glu Lys Leu Glu Phe
         35                  40                  45

ATC CTG GCT GCT TAC TGATAAGCTT GACCTGTGAA G                           180
Ile Leu Ala Ala Tyr
     50

```
(2) INFORMATION FOR SEQ ID NO: 10:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 10:

Gly Glu Phe Pro Lys Pro Ser Thr Pro Pro Gly Ser Ser Leu Thr Asp
 1               5                  10                  15

Thr Leu Gln Ala Glu Thr Asp Gln Leu Glu Asp Lys Lys Ser Ala Leu
                20                  25                  30

Gln Thr Glu Ile Ala Asn Leu Leu Lys Glu Lys Glu Lys Leu Glu Phe
            35                  40                  45

Ile Leu Ala Ala Tyr
            50

(2) INFORMATION FOR SEQ ID NO: 11:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
        (A) ORGANISM: synthetic, deduced from human sequences (ix) FEATURE:
        (A) NAME/KEY: CDS
        (B) LOCATION: 1..147
        (D) OTHER INFORMATION: /product= "intercalating peptide"
              /note= "gene cassete encoding intercalating
              jun-zipper and linker"

(ix) FEATURE:
        (A) NAME/KEY: misc_feature
        (B) LOCATION: 10..27
        (D) OTHER INFORMATION: /product= "synthetic linker"

(ix) FEATURE:
        (A) NAME/KEY: misc_feature
        (B) LOCATION: 28..147
        (D) OTHER INFORMATION: /product= "jun-zipper"

(xi) SEQUENCE DESCRIPTION: SEQ ID NO: 11:

GGT GAA TTC CCG TCT GGT AAC GAA GCT CGT ATC GCT CGT CTC GAG GAA       48
Gly Glu Phe Pro Ser Gly Asn Glu Ala Arg Ile Ala Arg Leu Glu Glu
 1               5                  10                  15

AAA GTT AAA ACC CTG AAA GCT CAG AAC TCC GAA CTG GCT TCC ACC GCT       96
Lys Val Lys Thr Leu Lys Ala Gln Asn Ser Glu Leu Ala Ser Thr Ala
                20                  25                  30

AAC ATG CTG CGT GAA CAG GTT GCT CAG CTG AAA CAG AAA GTT ATG AAC      144
Asn Met Leu Arg Glu Gln Val Ala Gln Leu Lys Gln Lys Val Met Asn
            35                  40                  45

TAC TGATAAGCTT GACCTGTGAA GTGAAAAATG GCG                             180
Tyr (2) INFORMATION FOR SEQ ID NO: 12:
```

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 12:

Gly Glu Phe Pro Ser Gly Asn Glu Ala Arg Ile Ala Arg Leu Glu Glu
 1               5                  10                  15

Lys Val Lys Thr Leu Lys Ala Gln Asn Ser Glu Leu Ala Ser Thr Ala
            20                  25                  30

Asn Met Leu Arg Glu Gln Val Ala Gln Leu Lys Gln Lys Val Met Asn
            35                  40                  45

Tyr (2) INFORMATION FOR SEQ ID NO: 13:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (v) FRAGMENT TYPE: N-terminal (vi) ORIGINAL SOURCE:
        (A) ORGANISM: synthetic, deduced from human sequences (ix) FEATURE:
        (A) NAME/KEY: CDS
        (B) LOCATION: 1..147
        (D) OTHER INFORMATION: /product= "intercalating peptide"
            /note= "gene cassette encoding intercalating
            fos-zipper and linker"

(ix) FEATURE:
        (A) NAME/KEY: misc_feature
        (B) LOCATION: 10..27
        (D) OTHER INFORMATION: /product= "synthetic linker"

(ix) FEATURE:
        (A) NAME/KEY: misc_feature
        (B) LOCATION: 28..147
        (D) OTHER INFORMATION: /product= "fos-zipper"

(xi) SEQUENCE DESCRIPTION: SEQ ID NO: 13:

GGT GAA TTC GGT CCG TCT GGT AAC GAA CTG ACC GAC ACC CTG CAG GCT        48
Gly Glu Phe Gly Pro Ser Gly Asn Glu Leu Thr Asp Thr Leu Gln Ala
 1               5                  10                  15

GAA ACC GAC CAG CTG GAA GAC AAA AAA TCC GCT CTG CAG ACC GAA ATC        96
Glu Thr Asp Gln Leu Glu Asp Lys Lys Ser Ala Leu Gln Thr Glu Ile
            20                  25                  30

GCT AAC CTG CTG AAA GAA AAA GAA AAA CTG GAA TTT ATC CTG GCT GCT       144
Ala Asn Leu Leu Lys Glu Lys Glu Lys Leu Glu Phe Ile Leu Ala Ala
            35                  40                  45

TAC TGATAAGCTT GACCTGTGAA GTGAAAAATG GCG                              180
Tyr (2) INFORMATION FOR SEQ ID NO: 14:

(i) SEQUENCE CHARACTERISTICS:
        (A) LENGTH: 49 amino acids
        (B) TYPE: amino acid -continued (D) TOPOLOGY: linear (ii) MOLECULE TYPE: protein (xi) SEQUENCE DESCRIPTION: SEQ ID NO: 14:

```
Gly Glu Phe Gly Pro Ser Gly Asn Glu Leu Thr Asp Thr Leu Gln Ala
 1               5                  10                  15

Glu Thr Asp Gln Leu Glu Asp Lys Lys Ser Ala Leu Gln Thr Glu Ile
            20                  25                  30

Ala Asn Leu Leu Lys Glu Lys Glu Lys Leu Glu Phe Ile Leu Ala Ala
            35                  40                  45

Tyr
```